(12) United States Patent
Ng et al.

(10) Patent No.: US 8,758,414 B2
(45) Date of Patent: Jun. 24, 2014

(54) BENDING TOOL AND METHOD FOR RESHAPING A BONE PLATE

(71) Applicant: Biomet Manufacturing, LLC, Warsaw, IN (US)

(72) Inventors: Ho-Kin Ng, Cooper City, FL (US); Priya Prasad, Miami, FL (US)

(73) Assignee: Biomet C.V., Gibraltar (GI)

( * ) Notice: Subject to any disclaimer, the term of this patent is extended or adjusted under 35 U.S.C. 154(b) by 0 days.

(21) Appl. No.: 14/026,068

(22) Filed: Sep. 13, 2013

(65) Prior Publication Data

US 2014/0012327 A1    Jan. 9, 2014

Related U.S. Application Data

(63) Continuation of application No. 12/579,949, filed on Oct. 15, 2009, now Pat. No. 8,551,107.

(51) Int. Cl.
*A61B 17/88*    (2006.01)
*A61B 17/58*    (2006.01)
*A61B 17/60*    (2006.01)
*A61F 2/00*    (2006.01)

(52) U.S. Cl.
USPC ............................................ 606/281; 606/101

(58) Field of Classification Search
USPC ................................ 606/86 B, 101, 281–284
See application file for complete search history.

(56) References Cited

U.S. PATENT DOCUMENTS 7,771,433 B2 *   8/2010   Orbay et al. .................. 606/101
8,337,506 B2 *   12/2012   Cunliffe et al. ............... 606/101

* cited by examiner

*Primary Examiner* — Andrew Yang
*Assistant Examiner* — Diana S Jones
(74) *Attorney, Agent, or Firm* — Harness, Dickey

(57) ABSTRACT

A bone plate system for reshaping a bone plate to conform to contours of bone surfaces. The system comprises a bone plate, a pair of spaced-apart guides removably attached to the bone plate, and a bending tool. The bending tool comprises a handle and a head attached to a distal end of the handle. The head defines a cavity sized and shaped to engage the pair of spaced-apart guides. The bone plate system is configured to transfer a leverage force applied by a user to the bending tool while the cavity of the head is fitted over the pair of spaced-apart guides to a regionalized bending moment to the bone plate through the pair of spaced-apart guides to reshape the bone plate.

4 Claims, 12 Drawing Sheets

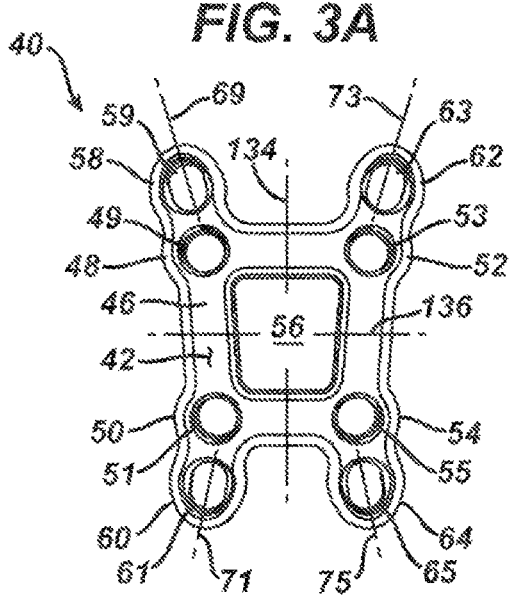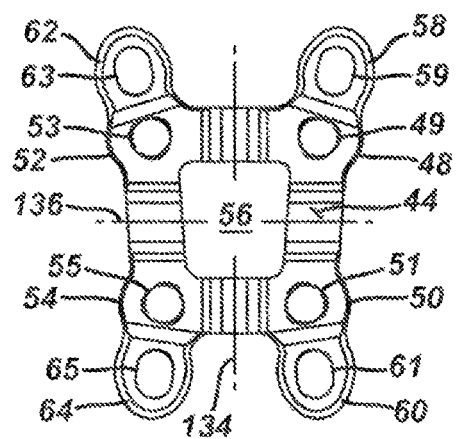

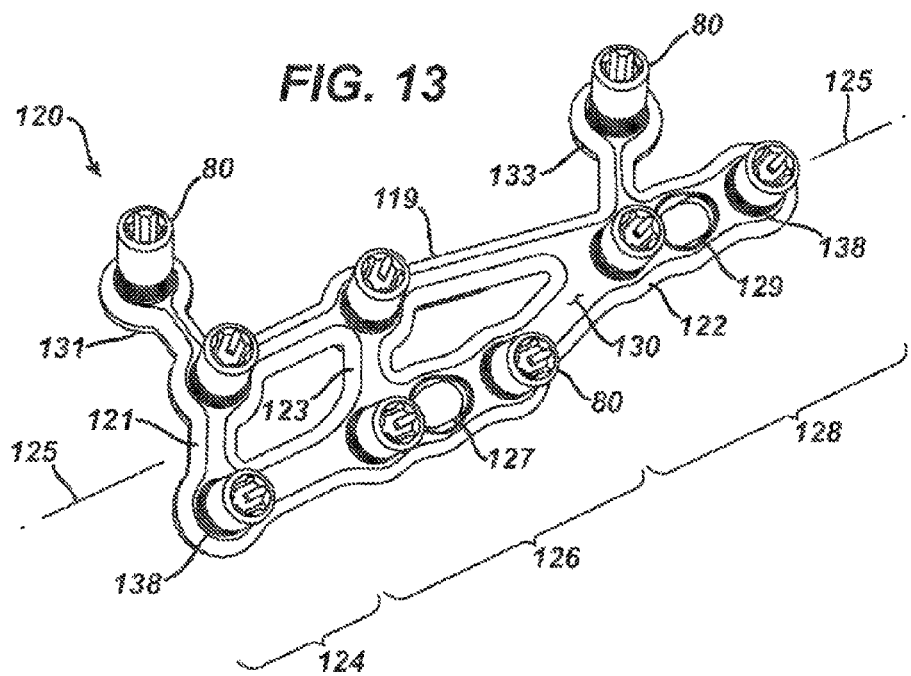
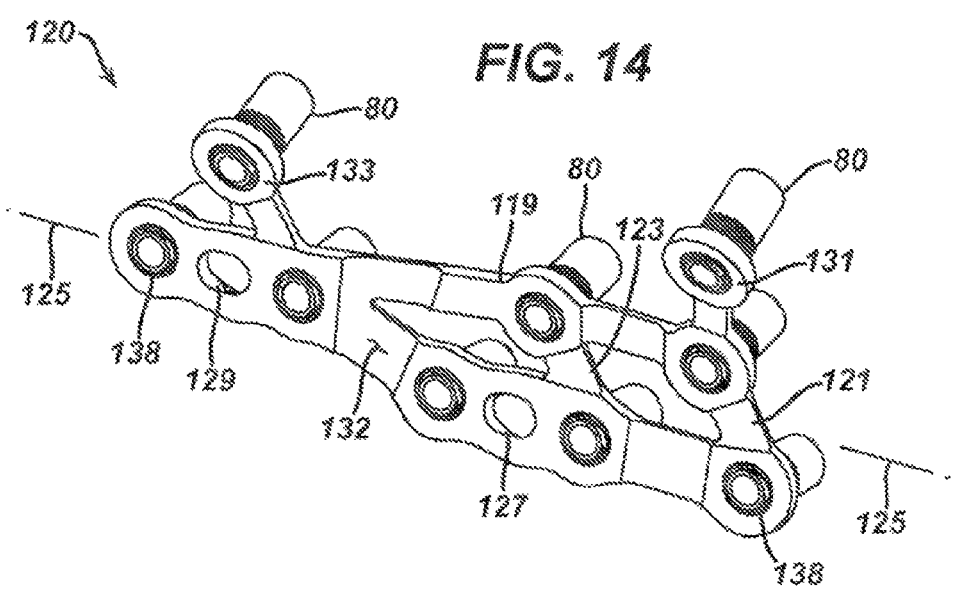

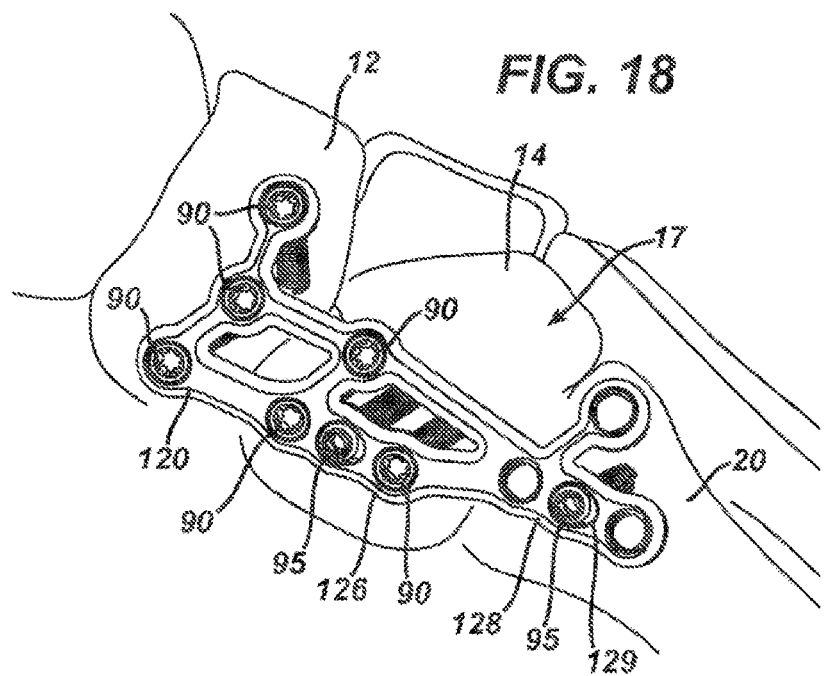
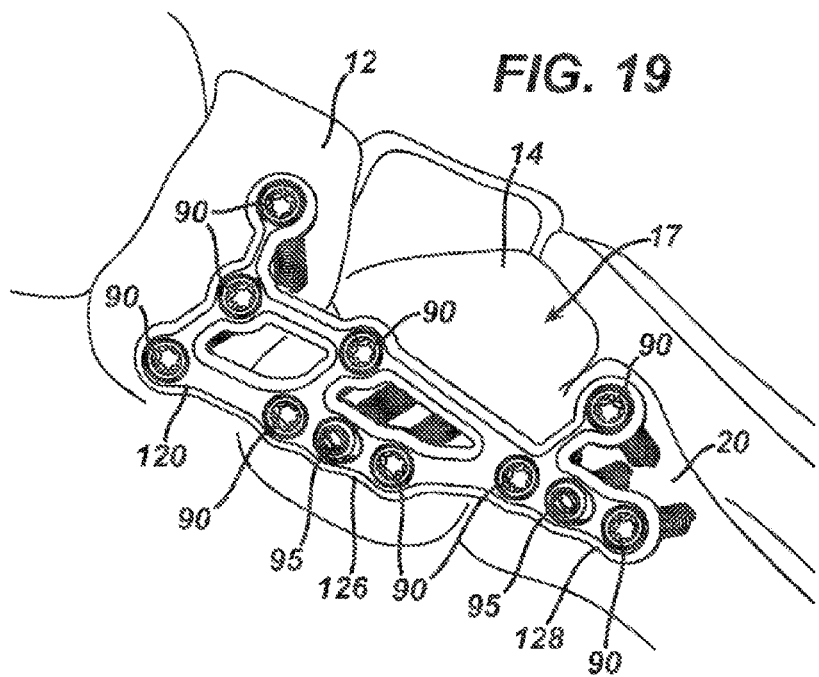

BENDING TOOL AND METHOD FOR RESHAPING A BONE PLATE

CROSS-REFERENCE TO RELATED APPLICATIONS

This application is a continuation of U.S. patent application Ser. No. 12/579,949 filed on Oct. 15, 2009. The entire disclosure of the above application is incorporated herein by reference.

FIELD

The present disclosure relates in general to orthopedic surgical devices and procedures, and more particularly, to internal fixation devices, instruments, and methods for the surgical correction of bones or for the repair of fractured bones of a patient.

BACKGROUND

Orthopedic surgeons are increasingly aware of the importance of properly treating midfoot fractures and dislocations, due partly to the more widespread use of CT and MRI scans. Even apparently simple avulsion fractures may be associated with significant joint damage that may lead to late pain. Since there is relatively little motion in the midfoot, successful fusion of the midfoot joints after fracture does not result in major disability. Therefore, a common surgical option for treating midfoot fractures and dislocations is fixation of adjacent bones using bone plates and/or screws.

Improvements to currently available bone plates for fusing the bones of the midfoot, as well as other bones of the foot, are needed for numerous reasons. For example, currently surgeons must first tightly draw together the bones of the midfoot before fixation with a bone plate. In some situations, it may be difficult for the surgeon to maintain the compression of bones until fixation, thereby resulting in undesirable gaps at the multi-directional, intersecting joint lines between the bones.

The following discloses novel implants, instruments, and methods for orthopedic surgery, which may be used in the bones of the foot or in other anatomies.

SUMMARY

This section provides a general summary of the disclosure, and is not a comprehensive disclosure of its full scope or all of its features.

In one aspect, the present disclosure provides a bone plate system for reshaping a bone plate to conform to contours of bone surfaces. The system comprises a bone plate, a pair of spaced-apart guides removably attached to the bone plate, and a bending tool. The bending tool comprises a handle and a head attached to a distal end of the handle. The head defines a cavity sized and shaped to engage the pair of spaced-apart guides. The bone plate system is configured to transfer a leverage force applied by a user to the bending tool while the cavity of the head is fitted over the pair of spaced-apart guides to a regionalized bending moment to the bone plate through the pair of spaced-apart guides to reshape the bone plate.

In another aspect, the bone plate system of the present disclosure comprises a bone plate defining at least four threaded holes, each threaded hole being preassembled with a guide removably attached thereto, thereby forming a first pair and a second pair of spaced-apart guides. A bending tool set is provided comprising two bending tools. A first bending tool has a first handle and a first head attached to a distal end of the first handle. The first head defines a first cavity sized and shaped to engage the first pair of spaced-apart guides. A second bending tool has a second handle and a second head attached to a distal end of the second handle. The second head defines a second cavity sized and shaped to engage the second pair of spaced-apart guides. The bone plate system is configured to transfer opposite leverage forces applied by a user to each of the bending tools to a regionalized bending moment to the bone plate through the first and second pairs of spaced-apart guides to reshape a region of the bone plate between the first and second pairs of spaced-apart guides.

In yet another aspect, the present disclosure provides a method for reshaping a bone plate to conform to contours of bone surfaces. The method comprises obtaining a bone plate system. The bone plate system includes a bone plate preassembled with a plurality of guides removably attached thereto. The bone plate system further includes first and second bending tools. Each bending tool comprises a handle and a head attached to a distal end of the handle. Each head defines a cavity configured to engage two of the guides. The method includes fitting the cavity of the first bending tool over a first pair of guides, and fitting the cavity of the second bending tool over a second pair of guides. Opposite leverage forces are applied to each handle of the first and second bending tools while each cavity is fitted over the respective pair of guides, thereby transferring a regionalized bending moment through the guides and into the bone plate to bend a region of the bone plate. The first and second bending tools are then removed from the respective pairs of guides.

BRIEF DESCRIPTION OF THE FIGURES

The following description and the accompanying drawings illustrate non-limiting examples of the invention. Unless otherwise indicated, like reference numerals identify the same elements.

FIG. 3A is a top view of the first bone plate;

FIG. 3B is a side view of the first bone plate;

FIG. 3C is an end view of the first bone plate;

FIG. 3D is a bottom view of the first bone plate;

FIG. 13 is a top perspective view of a second bone plate, shown assembled with a plurality of drill guides, for the fusion of the bones of the medial lateral column of the surgical patient's foot;

FIG. 14 is a bottom perspective view of the second bone plate of FIG. 13, shown assembled with the plurality of drill guides;

FIG. 18 shows the result of another step of the first fusion method, wherein the user partially attaches the second bone plate to the first metatarsal bone by the insertion of one compressing screw after the step of FIG. 17;

FIG. 19 shows the result of another step of the first fusion method, wherein the user fully attaches the second bone plate to the first metatarsal bone by the insertion of three locking screws after the step of FIG. 18, thereby completing the fusion of the medial column of the patient's foot;

DETAILED DESCRIPTION

Figure 1:
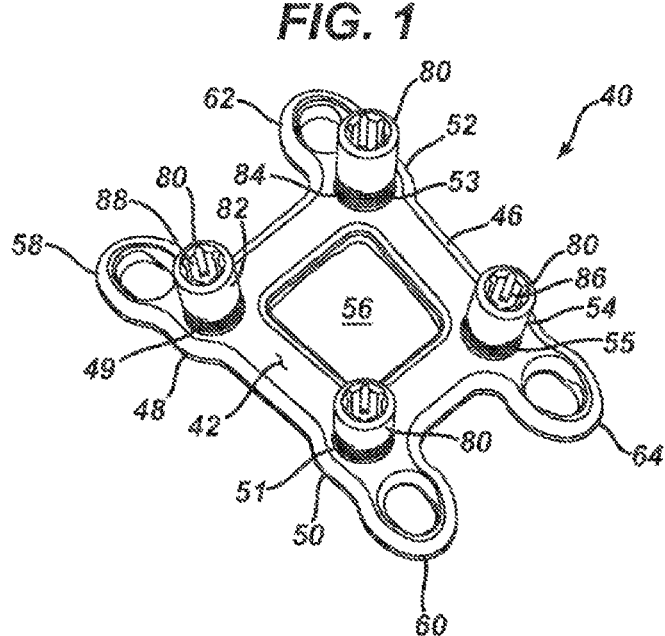
FIG. 1 is a top perspective view of a first bone plate, shown assembled with a plurality of drill guides, for fusion of the dorsal midfoot of the surgical patient.
Figure 4:
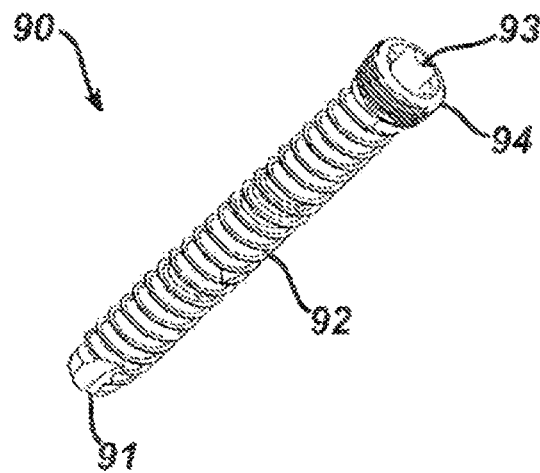
FIG. 4 is a perspective view of a locking screw.

FIG. 1 is a top perspective view of a first bone plate 40, as it may be provided by the manufacturer, shown preassembled with a plurality of drill guides 80. FIG. 4 shows a compressing screw 95 and a locking screw 93. A dorsal midfoot bone plate system may include first bone plate 40 preassembled with plurality of drill guides 80, a plurality of compressing screws 95 and a plurality of locking screws 93.

Figure 2:
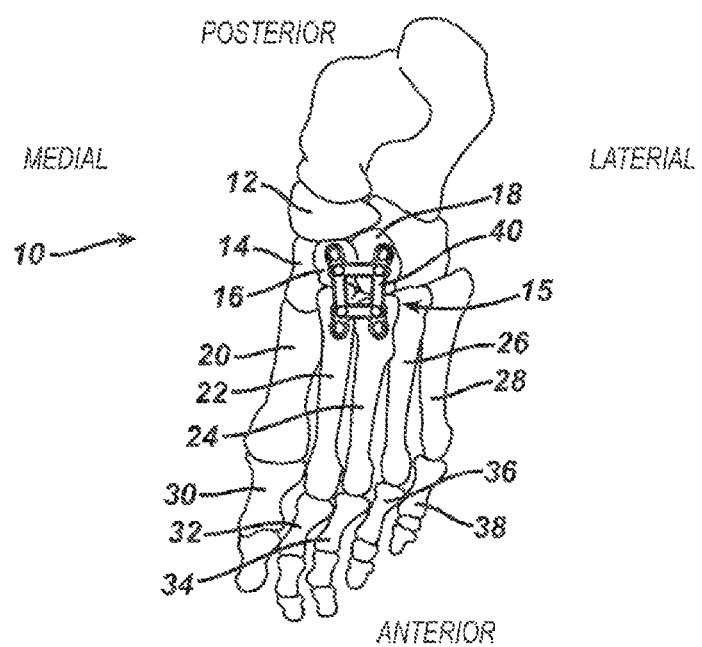
FIG. 2 is a dorsal view of the bones of the human foot, showing the first bone plate of FIG. 1, (shown without the drill guides for clarity) positioned on the dorsal midfoot.

FIG. 2 is a dorsal view of the bones of the human foot 10, showing first bone plate 40 positioned on the dorsal midfoot 15. FIG. 2 also indicates the conventional medical terms, "anterior, posterior, medial, lateral", as we shall refer to the sides of the human foot 10. The bones of the human foot 10 include the navicular tarsal bone 12, the first cuneiform 14, the second cuneiform 16, the third cuneiform 18, the first metatarsal 20, the second metatarsal 22, the third metatarsal 24, the fourth metatarsal 26, the fifth metatarsal 28, the first phalanges 30, the second phalanges 32, the third phalanges 34, the fourth phalanges 36 and the fifth phalanges 38. The dorsal midfoot 15 is formed by the convergence of the second cuneiform 16, the third cuneiform 18, the second metatarsal 22 and the third metatarsal 24.

FIGS. 3A, 3B, 3C and 3D are orthogonal views of first bone plate 40, which are described next in conjunction with FIG. 1. First bone plate 40 has a frame 46 that has a quadrilateral shape that defines a window 56, a top surface 42 and a bottom surface 44 that contacts the bone surfaces after implantation.

In this embodiment, frame 46 has an approximately square shape defining window 56. Frame 46 defines an anterior-posterior axis 134 (or A-P axis 134) and a medial-lateral axis 136 (or M-L axis 136).

Frame 46 has a first corner 48 containing a first threaded hole 49, a second corner 50 containing a second threaded hole 51, a third corner 52 containing a third threaded hole 53, and a fourth corner 54 containing a fourth threaded hole 55. Each of first, second, third and fourth threaded holes, 49, 51, 53 and 55 may be a tapered, multiple-lead, and internally threaded hole.

As may be viewed most easily in FIG. 3D, the thickness of first corner 48, second corner 50, third corner 52 and fourth corner 54 are approximately equal and may be greater than the portions of frame 46 connecting them to facilitate reshaping of first bone plate 40 during the surgical procedure.

Each of first, second, third and fourth threaded holes, 49, 51, 53 and 55 respectively, may be preassembled with one of the plurality of drill guides 80 threaded into the holes, an example of which is disclosed in U.S. Pat. No. 8,172,884. Each of the plurality of drill guides 80 facilitate drilling of a properly aligned pilot hole into the bone for receiving a locking screw 90 shown in FIG. 4.

As shown in FIG. 1, drill guide 80, includes a barrel portion 82 having a barrel diameter and a barrel length. For the drill guide embodiment shown herein, the barrel diameter may be approximately in the range of 2 mm to mm and barrel length may be approximately in the range of 5 mm to 10 mm. When drill guide 80 is preassembled to bone plate 40, the barrel portion extends above top surface 42. Drill guide 80 has a threaded portion 84 that threadably engages into any one of the threaded holes 49, 51, 53 and 55. Drill guide 80 has a through bore 86 that is coaxial with the threaded portion and sized to guide the drill bit required to drill the properly sized pilot hole. Drill guide 80 has a hex-shaped, drive socket 88 provided for insertion and removal of drill guide 80 into bone plate 40.

Those skilled in the art will recognize that it would also be possible to removably attach any one of numerous other types of threaded, cylindrical elements into any one of threaded holes 49, 51, 53 and 55. For example, a solid, threaded, cylindrical element such as a short screw with a cylindrical head may be removably attached to a threaded hole. Although such a cylindrical element does not have a through bore for guiding a drill, it may still be used in conjunction with a bending tool, such as the tool shown in FIG. 47 of US20090118768 to reshape bone plate 40.

Locking screw 90 includes a tapered, multiple-lead, externally threaded head 94 designed for threadable, locking engagement into any one of threaded holes 49, 51, 53 and 55. Locking screw has a drive socket 93, a threaded shank 92 for engagement into cortical bone, and a self-tapping tip 91. For the embodiment of locking screw 90 shown herein, threaded shank 92 may have a major diameter, for example, of 1.25 mm.

Still referring to FIGS. 1, 3A, 3B, 3C and 3D, first bone plate 40 further includes a first tab 58 extending from corner 48 and containing a first slot 59 having a first longitudinal axis 69, a second tab 60 extending from corner 50 and containing a second slot 61 having a second longitudinal axis 71, a third tab 62 extending from third corner 52 and containing a third slot 63 having a longitudinal axis 73, and a fourth tab 64 extending from corner 54 and containing a fourth slot 65 having a fourth longitudinal axis 75. Each of first longitudinal axis 69, second longitudinal axis 71, third longitudinal axis 73 and fourth longitudinal axis 75 is directed in the plane of frame 46 and approximately diagonally through window 56.

Figure 5:
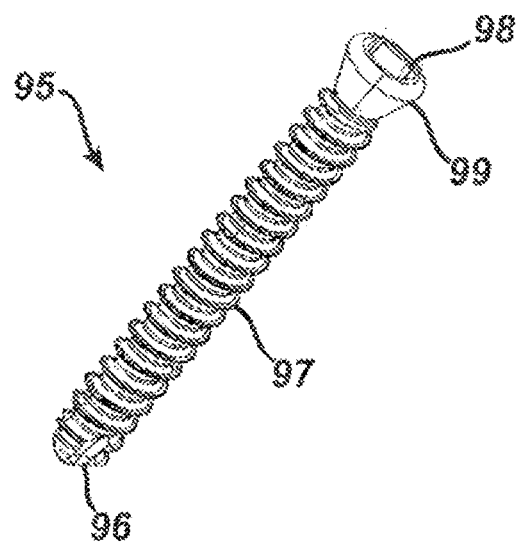
FIG. 5 is a perspective view of a compressing screw.

Each of first slot 59, second slot 61, third slot 63 and fourth slot 65 may receive a compressing screw 95, which is shown in FIG. 5. As will be described, compressing screw 95 may be used to move bone parts together prior to inserting additional locking screws to complete attachment of the bone plate to the bone parts. Compressing screw 95 may be formed from a variety of metal alloys, such as Ti6Al4V, and includes a smooth conical head 99 having a drive socket 98, a threaded shank 97 for engagement into cortical bone, and a self-tapping tip 96. Threaded shank 97 may, for example, have a major diameter of 1.25 mm.

First bone plate 40 may be formed from a titanium alloy, a stainless steel or any one of a number of biocompatible materials well-known in the art. The manufacturing processes for forming first bone plate 40 are also well-known, although the exact processes may vary to provide desired mechanical properties such as the ability to be reshaped during the surgical procedure to conform to the bone surfaces.

Figure 6:
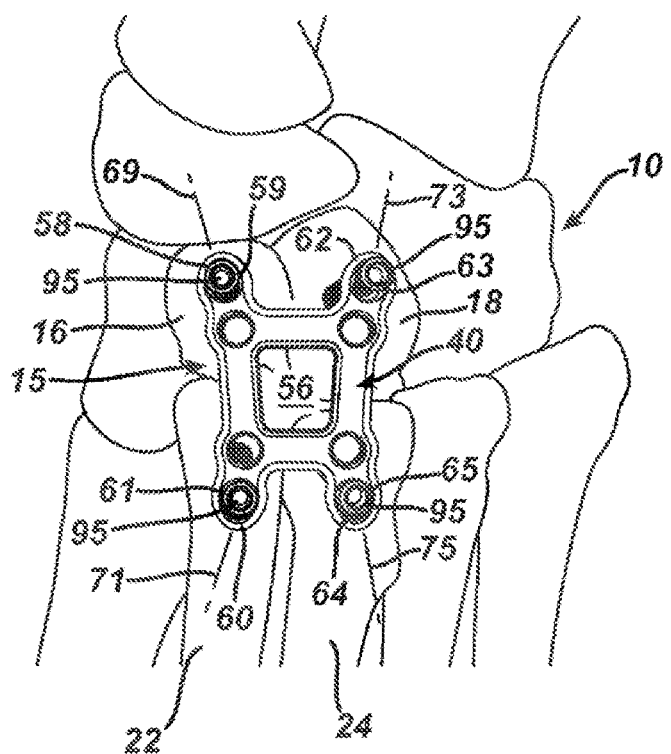
FIG. 6 is a top view of the first bone plate partially attached to the bones of the dorsal midfoot using four compressing screws.
Figure 7:
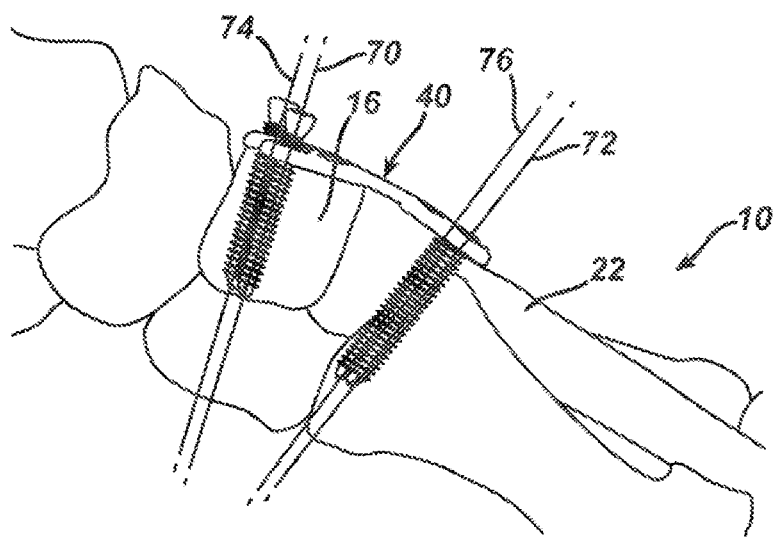
FIG. 7 is a side view of the first bone plate, compressing screws and bones of the dorsal midfoot shown in FIG. 6.

The user may attach first bone plate 40 onto the bones of the dorsal midfoot 15 as described next in conjunction with FIGS. 6, 7 and 8. FIG. 6 is a top view and FIG. 7 is a side view showing first bone plate 40 partially attached to the bones of the dorsal midfoot 15 using four compressing screws 95. One compressing screw 95 passes through first slot 59 and threadably engages into the second cuneiform 16; one compressing screw 95 passes through second slot 61 and threadably engages into the second metatarsal 22; one compressing screw 95 passes through third slot 63 and threadably engages into the third cuneiform 18; one compressing screw 95 passes through fourth slot 65 and threadably engages into the third metatarsal 24.

To achieve the result shown in FIGS. 6 and 7, the user may first make an incision over the bones of the dorsal midfoot 15, retract the soft tissues and then place first bone plate 40 onto the dorsal midfoot 15, such that window 56 approximately centers over the junction of the four bones of the dorsal midfoot 15. The user may choose to reshape first bone plate 40 (as will be described later for FIGS. 11 and 12) until first bone plate 40 conforms closely to the contours of the surfaces of the bones. To insure good screw engagement into bone and implantation of a robust construct, the user may position first tab 58 over the second cuneiform 12, second tab 60 over the second metatarsal 22, third tab 62 over the third cuneiform 18 and fourth tab 64 over the third metatarsal 24.

Next, one at a time, the user may drill each pilot hole and then partially insert each compressing screw 95 until all four compressing screws are partially engaged into the four bones of the dorsal midfoot 15. The user may then gradually tighten each of the four compressing screws 95 alternately until each is snuggly engaged into the underlying bone. Each of first slot 59, second slot 61, third slot 63 and fourth slot 65 are oriented diagonally as described for FIG. 3A, such that fully inserting each compressing screw 95 in the respective slot urges movement of the attached underlying bone approximately inwardly against the other three bones of the dorsal midfoot 15. Therefore, upon full insertion of the four compressing screws 95, the four bones of the dorsal midfoot 15 are dynamically compressed inwardly together, simultaneously in both the anterior-posterior direction and the medial-lateral direction. This type of compression, also referred to as "multi-axial compression", as opposed to axial compression provided by previous bone plates, helps the user to achieve minimal spacing between the four bone parts so that the bone parts may fuse together. Those skilled in the art will now envision other possible types of bone plates incorporating multi-axial compression for drawing together multiple bone parts of various types, including whole bones and bone fragments of fractured bones.

Figure 8:
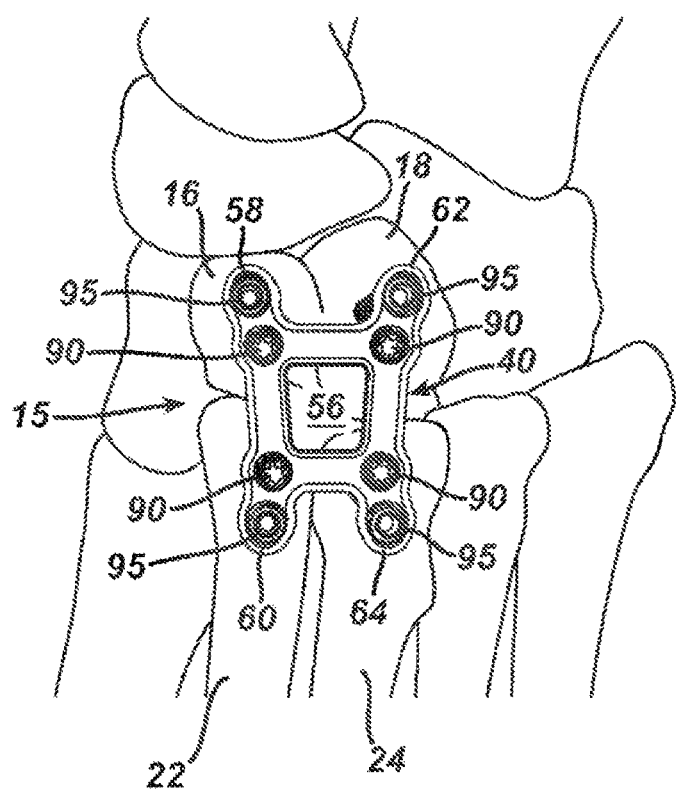
FIG. 8 is a top view of the first bone plate fully attached to the bones of the dorsal midfoot using four compressing screws and four locking screws.

Once the four compressing screws 95 are fully inserted, the user may drill four pilot holes and insert four locking screws 90 as shown in FIG. 8, thereby completing the fusion of the bones of the dorsal midfoot 15.

For clarity, FIGS. 6 and 7 do not show the first plurality of drill guides 80 preassembled into first bone plate 40, such as is shown in FIG. 2. Clearly, it is possible to use a handheld drill guide to drill each of the pilot holes for the four locking screws 90. However, preassembled drill guides 80 as shown in FIG. 2 provides numerous advantages. One advantage is that providing the first plurality of drill guides 80 preassembled to first bone plate 40 enables the user to reshape first bone plate 40 in vivo, as will be described next.

The method just described is one of a number of possible method embodiments for attaching first bone plate 40 to the bones of the dorsal midfoot. For example, in an alternate method embodiment, the user may prepare the surgical site and position first bone plate 40 on the bones of the dorsal midfoot as previously described. Next the user may fully insert a pair of compressing screws 95 on one side of plate 40 and then fully insert a pair of locking screws 90 on the same side of plate 40. Next the user may fully insert a pair of compressing screws 95 on the opposite side of plate 40 and then fully insert a pair of locking screws 90 on that side of plate 40.

Figure 9:
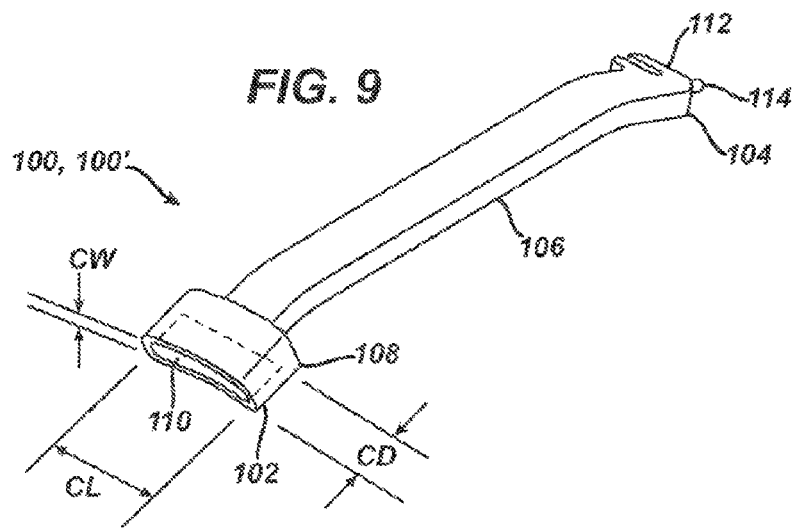
FIG. 9 is a top perspective view of a bending tool.
Figure 10A:
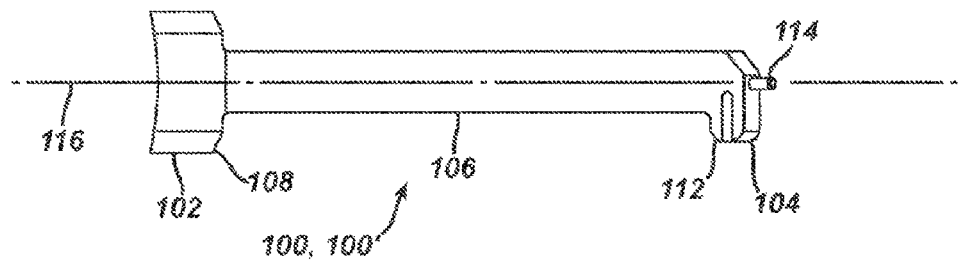
FIG. 10A is a bottom view of the bending tool of FIG. 9.
Figure 10B:
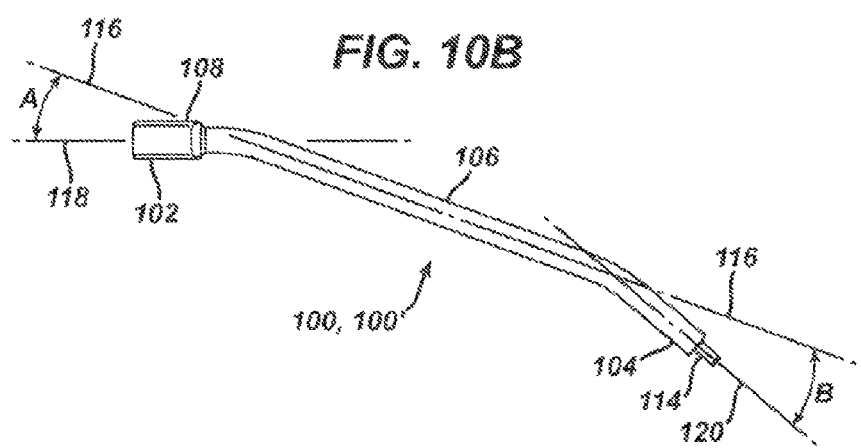
FIG. 10B is a side view of the bending tool of FIG. 9.

FIG. 9 is a top perspective view, FIG. 10A is a bottom view and FIG. 10B is a side view of a first bone plate bending tool 100 that includes a distal end 102, a proximal end 104 and a longitudinal axis 116 extending therebetween. First bending tool 100 further includes a distal head 108 that is attached to distal end 102 of a handle 106. Distal head 108 has a cavity 110 sized and shaped to fit over a pair of adjacent drill guides 80, wherein the axes defined by bore 86 of each drill guide 80 are approximately parallel.

As labeled in FIG. 9, cavity 100 has a cavity length (CL), a cavity width (CW) and a cavity depth (CD). The cavity width is slightly greater than the barrel diameter of drill guide 80. The cavity length is greater than the sum of twice the barrel diameter and the separation distance between the adjacent drill guides 80. The cavity depth may be, for example, at least half of the barrel length of drill guide 80 to provide ample engagement of cavity 100 to the adjacent pair of drill guides 80 to transmit a high leverage force without slipping apart. To insure maximum engagement, the cavity depth may be equal to or greater than the barrel length.

Figure 11:
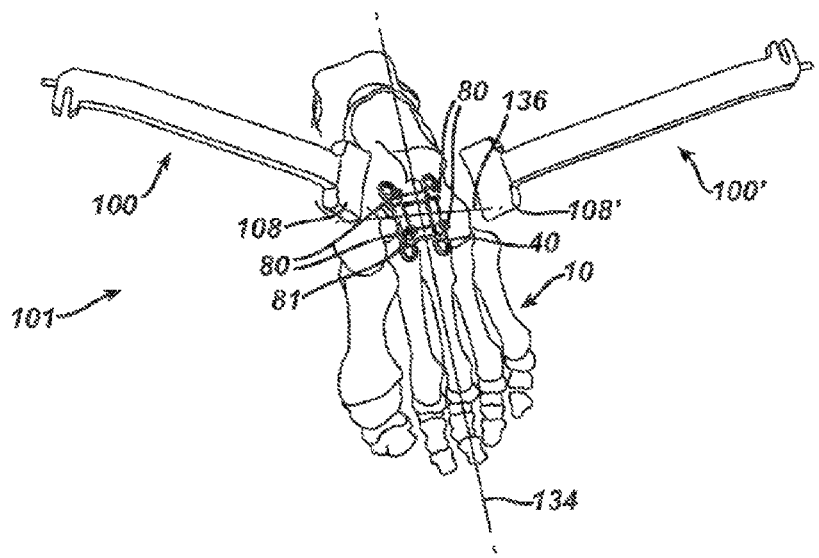
FIG. 11 shows an opposing pair of bending tools oriented for placement onto the drill guides preassembled to the first bone plate, which has been initially positioned on the bones of the dorsal midfoot.
Figure 12:
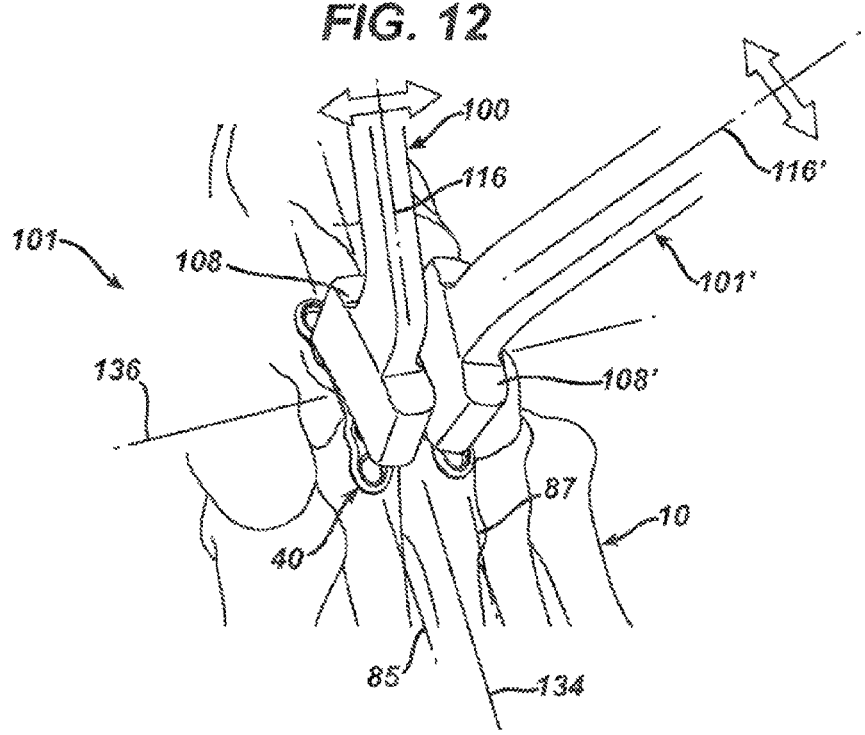
FIG. 12 shows the opposing pair of bending tools placed onto the drill guides preassembled to the first bone plate, such that a user may apply a leverage force to the bending tools to transmit a bending moment to the first bone plate to reshape it about its anterior-posterior axis.

A bone tool set may include a second bending tool 100' that is identical to first bending tool 100. FIGS. 11 and 12 depict how the user may use bending tool set 101 to reshape first bone plate 40 about AP axis 134. First bending tool 100 may be fitted over a first pair 81 of drill guides 80, and second bending tool 100' may be fitted over a second pair 83 of drill guides 80, wherein the first pair 81 and second pair 83 are preassembled to bone plate 40 on opposing sides of the region of bone plate 40 to be bent. As shown in FIG. 12, first pair 81 defines a first pair axis 85 and second pair 83 defines a second pair axis 87, which is approximately parallel to first pair axis 85.

As shown in FIG. 12 and indicated by arrows, the user may apply a leverage force to bending tool 100 in a direction that is approximately perpendicular to first pair axis 85 and an equal and opposite leverage force to bending tool 100' in a direction that is approximately perpendicular to second pair axis 87. In this way, the user may controllably transmit a sufficient bending moment into the region of bone plate 40 between first pair 81 and second pair 83 to bend bone plate 40 about A-P axis 134, thereby reshaping bone plate 40 to conform more closely to the contours of the underlying bone surfaces. Alternately, the user may use bending tool set 101 to bend first bone plate 40 about M-L axis 136, in which case, first pair 81 would include the two drill guides 80 anterior to M-L axis 136 and second pair 83 would include the two drill guides 80 posterior to M-L axis 134.

Tool 100 and second tool 100' may be used to reshape bone plate 40 already positioned onto the bone site as shown in FIGS. 11 and 12, or may be used to reshape bone plate 40 outside of the patient's body. The user may use the pair of tools 100, 100' to bend first bone plate 40 about the A-P axis 134, as shown in FIGS. 11 and 12.

In some situations, it may also be possible for the user to apply a leverage force to first bending tool 100 fitted over first pair 81 of drill guides 80, while holding bone plate 40 by hand or against a relatively immovable, sterile surface, for example.

Using bending tool set 101 enables the user to apply a regionalized bending moment to the bone plate. This may reduce the number of tool applications required to reshape the bone plate, reduce surgical time, and help create a desired, uniform bend about an axis of the bone plate. In addition, using each bending tool to apply the leverage force to a pair of adjacent drill guides (or other types of cylindrical elements inserted into the threaded holes, as noted earlier). Compared to engagement with a single drill guide, by applying force to more than one drill guide the stress magnitude is significantly reduced at the threaded engagement between each drill guide and corresponding threaded hole. This may allow the user to apply much greater leverage force to the bending tools, so that it is possible to bend significantly stiffer bone plates.

Bending tool 100 may further include a proximal end effector 112 and a proximal post 114. Distal end 102 defines a distal axis 118 that may form an angle "A" with longitudinal axis 116. Proximal end 104 defines a proximal axis 120 that may form an angle "B" with longitudinal axis 116. The angles "A" and "B" facilitate access and visualization to the surgical wound site during use and the ergonomic application of hand force. Tool 100 may be formed from a stainless steel or any one of many other rigid, biocompatible materials that are commonly used for surgical instruments.

Still referring to FIGS. 9, 10A and 10B, proximal end effector 112 of tool 100 may include a slot 113 that is sized and shaped to fit closely over the thickness of first bone plate 40. Similarly, tool 100' includes a similar, proximal end effector and slot, such that the pair of tools 100, 100' may also be used like a pair of conventional, surgical bending irons that are well-known in the art.

Post 114 is sized and shaped to fit into the bore of drill guide 80, thereby enabling the user another way to apply force individually to any one of drill guides preassembled to first bone plate 40. Using post 114 of tool 100 in opposition to tool 100' having a post 114' (not shown) enables the user to apply a directed bending force to first bone plate 40, such as may be useful for "tweaking" the final, desired shape of first bone plate 40.

Proximal end effector 112 and post 114 also enable the user to use tool 100 on other bone plates that are preassembled with drill guides 80, but that do not have a pair of drill guides properly spaced for use with distal head 108.

FIG. 13 is a top perspective view and FIG. 14 is a bottom perspective view of a second bone plate 120, shown preassembled with a plurality of drill guides 80. A medial column fusion system for fusing the bones of the medial column (inside) of the surgical patient's foot includes second bone plate 120 that is preassembled with plurality of drill guides 80, a plurality of compressing screws 95 and a plurality of locking screws 93.

Figure 15:
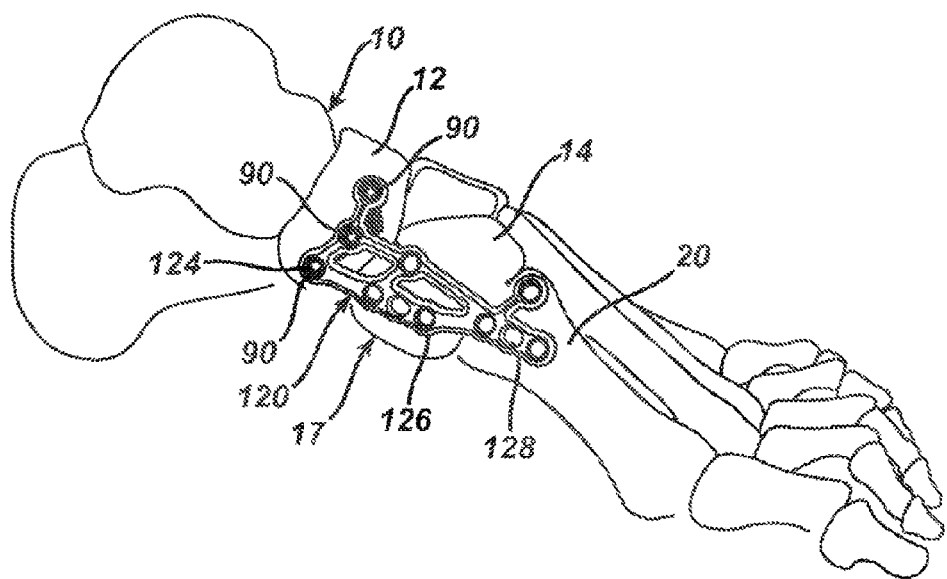
FIG. 15 is a medial view of the human foot 10 and shows the result of a step of a first fusion method, wherein the user attaches the second bone plate to the navicular tarsal bone by insertion of three locking screws.

FIG. 15 shows the result of a step of a first fusion method and illustrates the positioning of second bone plate 120 on the medial column 17 of foot 10. The medial column 17 is formed by a series of three bones of the inner foot: the navicular tarsal 12, the first cuneiform 14 and the first metatarsal 20.

As shown in FIGS. 13 and 14, second bone plate 120 has a generally elongated shape defining a longitudinal axis 125, a top surface 130 and a bottom surface 132 for contact against the underlying bones of the medial column 17. Second bone plate 120 includes a body element 122 and an arm element 119 extending from body element 122. Arm element 119 and body element 122 extend nearly parallel to each other along opposite sides of longitudinal axis 125. A first span element 121 and a second span element 123 bridge between arm element 119 and body element 122.

As shown in FIG. 13, second bone plate 120 has three longitudinal portions that correspond to the underlying bones to which they are to be attached: a tarsal portion 124, a cuneiform portion 126 and a metatarsal portion 128. A first tab 131 extends transversely from tarsal portion 124 and a second tab 133 extends transversely from metatarsal portion 128. As shown in FIG. 14, portions of arm element 119, body element 122, first span 121, second span 123, first tab 131 and second tab 133 have a smaller thickness than the thickness of the rest of second bone plate 120 to facilitate bending in those regions for reshaping second bone plate 120 to conform to the contours of the underlying bone surfaces.

Second bone plate 120 includes a plurality of threaded holes 138, each of which may be identical to threaded holes 49, 51, 53 and 55 of first bone plate 40 (FIG. 1). Each of tarsal portion 124, cuneiform portion 126 and metatarsal portion 128 may include at least one threaded hole 138 preassembled with drill guide 80, although for the embodiment shown in FIGS. 13 and 14, each portion has three threaded holes preassembled with three drill guides 80. Cuneiform portion 126 also includes a first slot 127 and metatarsal portion 128 also includes a second slot 129. First slot 127 and second slot 129 may be identical to slots 59, 61, 63 and 65 of first bone plate 40 and may be used with compressing screw 95 (FIG. 5). First slot 127 and second slot 129 are configured and oriented to provide axial compression in a direction towards tarsal portion 124 and approximately parallel to longitudinal axis 125.

Drill guides 80 provide for drilling coaxially aligned pilot holes for bone screws into the bone. The user also may use drill guides 80 in combination with one or an opposing pair of bending tools, such as first bending tools 100 and second bending tool 100', to reshape bone plate 120. As previously noted, the user may insert post 114 of first and second bending tools 100, 100' into bore 86 of drill guides 80 and apply a leverage force to transmit a bending moment into bone plate 120. It is also possible to use other types of bending tools, including without limitation bending irons that engage a single drill guide or bending tools that directly engage the plate.

As described previously for first bone plate 40, second bone plate 120 may be formed from a variety of metal alloys, such as Ti6Al4V, or any one of a number of biocompatible materials commonly used for the construction of bone plates using conventional manufacturing techniques, although some variations of manufacturing techniques may be employed to provide specific mechanical properties.

Two surgical methods are described next for fusing the bones of the medial column of the foot using the medial column fusion system. In a first fusion method, the navicular tarsal 12 and the first cuneiform 14 are first drawn together and then the first metatarsal 20 is drawn against the first cuneiform 14. In a second fusion method, the navicular tarsal 12 and the first metatarsal 20 are drawn together while the first cuneiform 14 is permitted to move with the first metatarsal 20.

Figure 20:
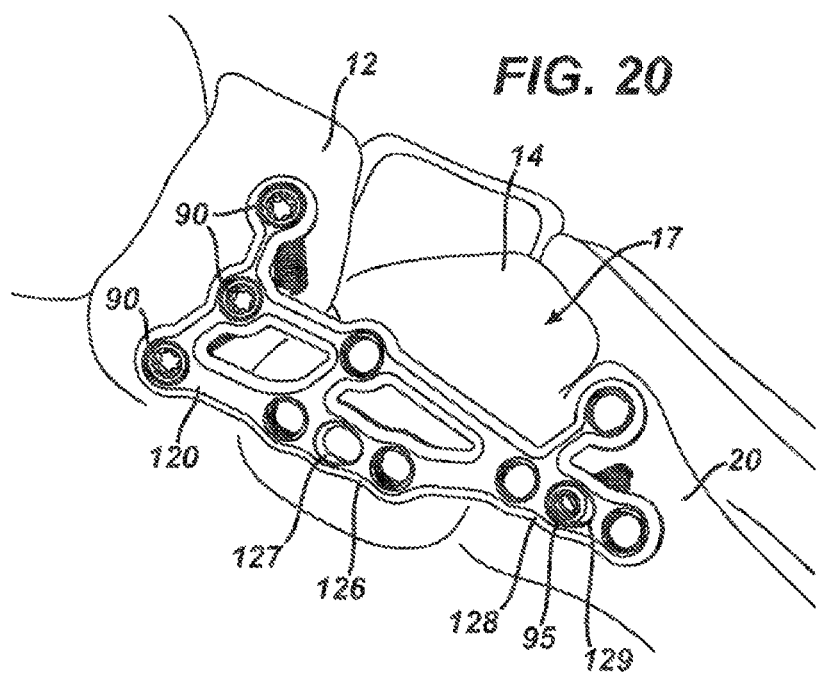
FIG. 20 shows the result of a step of a second fusion method, wherein the user partially attaches the second bone plate to the metatarsal by the insertion of one compressing screw after the step of FIG. 15.
Figure 21:
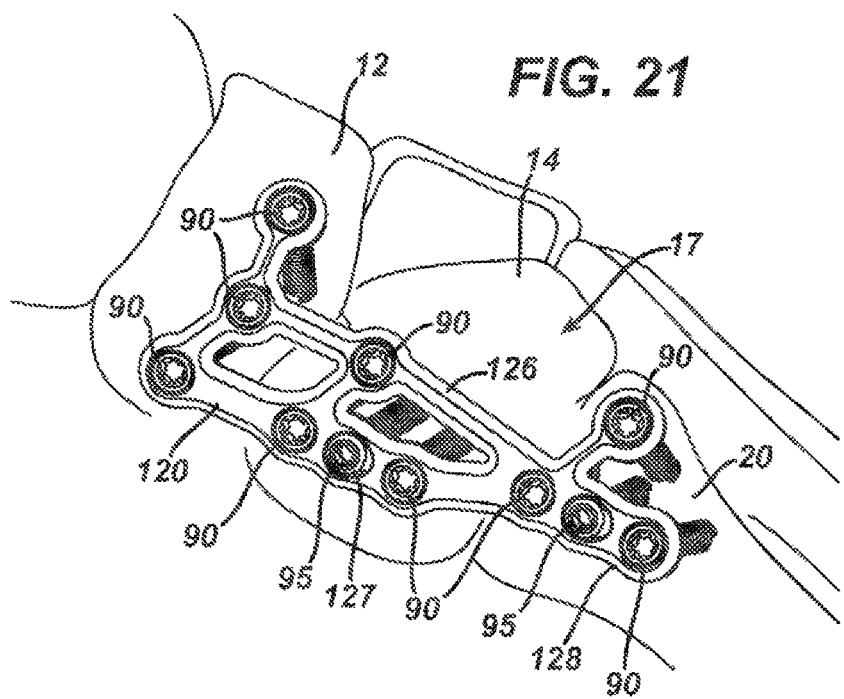
FIG. 21 shows the result of a number of steps of the second fusion method, wherein the user completes the attachment of the second bone plate to the bones of the medial column after the step of FIG. 20.

FIGS. 15-19 depict the results of steps included in the first fusion method. FIGS. 15, 20 and 21 depict the results of steps included in the second fusion method.

FIGS. 15-21 show second bone plate 40 without preassembled drill guides 80. For the steps of the first and second fusion methods described next, it should be understood that insertion of locking screw 90 includes drilling a pilot hole into bone with either drill guide 80 preassembled to second bone plate 120, a conventional handheld drill guide or without any type of drill guide, although the latter is likely to result in binding of the screw being inserted if the pilot hole in the bone is not coaxial with the threaded hole of the plate. However, providing second bone plate 120 with preassembled drill guides 80 enables the user to perform the surgical procedure more quickly and more accurately than if using a handheld drill guide and also provides the ability to reshape the bone plate using bone shaping tools as previously described. When using second bone plate 120 with preassembled drill guides 80, each drill guide 80 should be removed from second bone plate 120 after drilling the pilot hole.

Similarly, for the steps of the first and second fusion methods described next, it should be understood that insertion of compressing screw 95 includes drilling a pilot hole into bone.

The first steps for both the first and second fusion methods include incising the soft tissues overlying the medial column 17 of the foot 10 and retracting the soft tissues to expose the bones of the medial column.

The next step of both the first and second fusion methods is depicted in FIG. 15 in which the user attaches second bone plate 120 to the navicular tarsal 12. The user inserts at least one locking screw 94 through tarsal portion 124 of second bone plate 120 and into the navicular tarsal 12, although for this embodiment of second bone plate 120, the user may insert up to three locking screws 94 through tarsal portion 124 and into the navicular tarsal 12.

Figure 16:
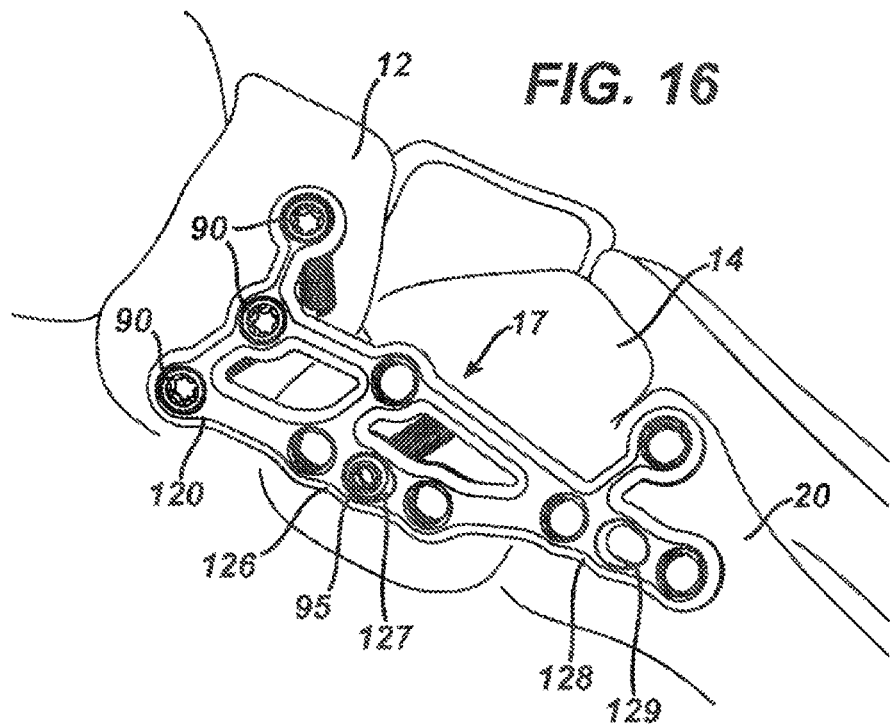
FIG. 16 shows the result of another step of the first fusion method, wherein the user partially attaches the second bone plate to the first cuneiform bone by the insertion of one compressing screw after the step of FIG. 15.
Figure 17:
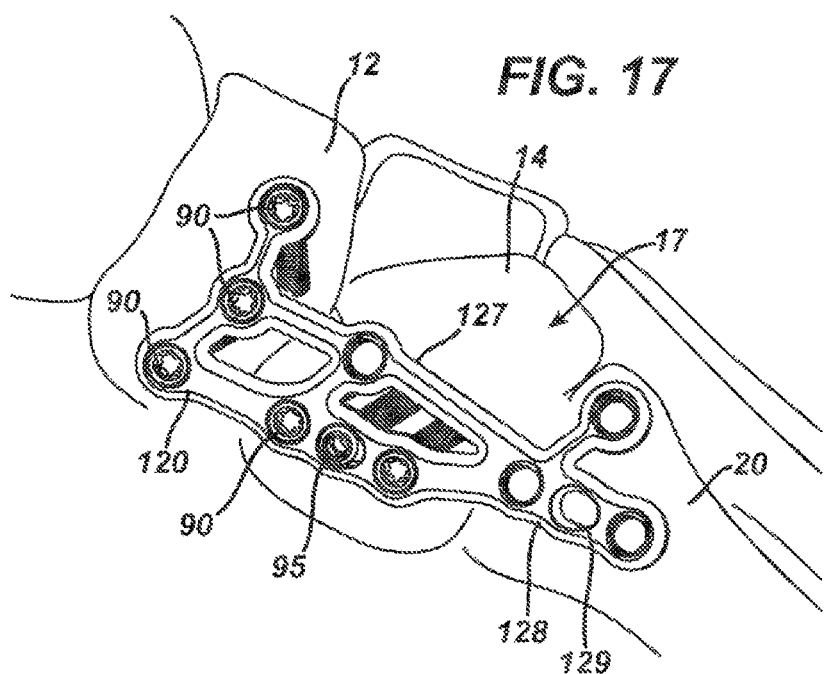
FIG. 17 shows the result of another step of the first fusion method, wherein the user fully attaches the second bone plate to the first cuneiform bone by the insertion of three locking screws after the step of FIG. 16.

The remaining steps of the first fusion method include the following: The user partially attaches second bone plate 120 to the first cuneiform 14 by the insertion of one compressing screw 95 through first slot 127 of cuneiform portion 126 of second bone plate 140 and into the underlying cuneiform 14 (FIG. 16). This step axially compresses cuneiform 14 against navicular tarsal 12. Then the user inserts at least one locking screw 90 through cuneiform portion 127 of second bone plate 120 and into cuneiform 14, although for this embodiment of second bone plate 120, the user may insert up to three locking screws 90 (FIG. 17) through cuneiform portion 126. Next the user inserts compressing screw 95 through second slot 129 of metatarsal portion 128 of second bone plate 120 and into the metatarsal 20 (FIG. 18). This step axially compresses the metatarsal 20 against the cuneiform 14. Next the user completes the fusion of medial column 17 by inserting at least one locking screw 90 through metatarsal portion 128 of second bone plate 120 and into the metatarsal 20 (FIG. 19), although for this embodiment the user may insert up to three locking screws 90 through metatarsal portion 128.

The remaining steps of the second fusion method (after performing the step depicted in FIG. 15) include the following: The user inserts compressing screw 95 through second slot 129 of second bone plate 120 and into the metatarsal 20 (FIG. 20). The user then inserts at least one locking screw 90 through metatarsal portion 128 of second bone plate 120 and into the metatarsal 20. For this embodiment, the user may insert up to three locking screws 90 through metatarsal portion 128 (FIG. 21). Next the user inserts compressing screw 95 through slot 127 of cuneiform portion 126 and into cuneiform 14. For this step, the user may choose to insert compressing screw 95 into a "neutral", central portion of slot 127, such that the head of screw 95 does not forcefully interact with slot 127. This is because the desired compression of the bones was already achieved by the insertion of compressing screw 95 in second slot 129. Finally, the user inserts at least one locking screw 90 through cuneiform portion 126 of second bone plate 120 and into the cuneiform 14, although for this embodiment the user may insert up to three locking screws 90 through cuneiform portion 126.

For both the first and second fusion methods, after the user has completed the attachment of second bone plate 120 to the medial column 17, the user finally closes the incision using conventional techniques for this type of surgical procedure.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For example, the specific materials, dimensions, and the scale of drawings will be understood to be non-limiting examples. As a further example, the foregoing disclosure included many examples of foot anatomy, but the teachings of this disclosure may also be used for bones of other anatomies. Accordingly, the scope of the present invention should be considered in terms of the following claims and is understood not to be limited to the details of structure, materials, or acts shown and described in the specification and drawings.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for reshaping a bone plate to conform to contours of bone surfaces, the method comprising:
    obtaining a bone plate system comprising:
        a bone plate preassembled with a plurality of guides removably attached thereto; and
        first and second bending tools, each bending tool comprising a handle and a head attached to a distal end of the handle, each head defining a cavity configured to engage two of the plurality of guides;
    fitting the cavity of the first bending tool over a first pair of guides and fitting the cavity of the second bending tool over a second pair of guides;
    applying opposite leverage forces to each handle of the first and second bending tools while each cavity is fitted over the respective pair of guides, thereby transferring a regionalized bending moment through the guides and into the bone plate to bend a region of the bone plate; and
    removing the first and second bending tools from the respective pairs of guides.

2. The method of claim 1, comprising positioning the bone plate on a surface of the bones of a surgical patient while reshaping the bone plate.

3. The method of claim 1, comprising simultaneously applying equal and opposite leverage forces to each handle of the first and second bending tools.

4. The method of claim 1, wherein the bone plate defines a plurality of threaded screw holes, each of the plurality of threaded screw holes being preassembled with one of the plurality of guides.

* * * * *